(12) United States Patent
Fransson et al.

(10) Patent No.: US 8,174,262 B2
(45) Date of Patent: May 8, 2012

(54) FLUID SATURATION ESTIMATION

(75) Inventors: Carl-Magnus Fransson, Cleveland, TX (US); Kaarina T. Fransson, legal representative, Skovde (SE); Ridvan Akkurt, Dhahran (SA)

(73) Assignee: Halliburton Energy Services, Inc., Houston, TX (US)

( * ) Notice: Subject to any disclaimer, the term of this patent is extended or adjusted under 35 U.S.C. 154(b) by 178 days.

(21) Appl. No.: 12/374,451

(22) PCT Filed: Jul. 21, 2006
(Under 37 CFR 1.47)

(86) PCT No.: PCT/US2006/028621
§ 371 (c)(1),
(2), (4) Date: Aug. 31, 2010

(87) PCT Pub. No.: WO2008/010810
PCT Pub. Date: Jan. 24, 2008

(65) Prior Publication Data
US 2011/0043202 A1 Feb. 24, 2011

(51) Int. Cl.
*G01V 3/00* (2006.01)
(52) U.S. Cl. .................... 324/303; 324/300
(58) Field of Classification Search ............ 324/300, 324/303, 306; 703/5, 9, 10, 12; 702/1–2, 702/6–9, 11–13; 73/152.28
See application file for complete search history.

(56) References Cited

U.S. PATENT DOCUMENTS

| | | | | |
|---|---|---|---|---|
| 6,392,409 | B1 * | 5/2002 | Chen | 324/303 |
| 6,600,316 | B2 * | 7/2003 | Chen et al. | 324/303 |
| 6,808,028 | B2 * | 10/2004 | Woodburn et al. | 175/48 |
| 7,755,354 | B2 * | 7/2010 | Akkurt | 324/303 |
| 7,804,297 | B2 * | 9/2010 | Romero | 324/303 |
| 2010/0228485 | A1 * | 9/2010 | Betancourt et al. | 702/13 |
| 2010/0277167 | A1 * | 11/2010 | Romero | 324/303 |
| 2010/0283459 | A1 * | 11/2010 | Kruspe et al. | 324/303 |

FOREIGN PATENT DOCUMENTS

| | | |
|---|---|---|
| WO | WO-2004/032257 A1 | 2/2004 |
| WO | WO-2005/104587 A1 | 5/2005 |

OTHER PUBLICATIONS

Akkurt, R., et al., "Fluid Sampling and Interpretation with the Downhole NMR Fluid Analyzer", *SPE 90971*, (2004),1-13.
Bouton, J., et al., "Assessment of Sample Contamination by Downhole NMR Fluid Analysis", *SPE 71714*, (2001),1-10.
"International Search Report for Application No. PCT/US2006/028621, date mailed Apr. 17, 2007", 5 pgs.
"Written Opinion of the International Searching Authority for Application No. PCT/US2006/028621, date mailed Apr. 17, 2007", 4 pgs.

* cited by examiner

*Primary Examiner* — Brij Shrivastav
(74) *Attorney, Agent, or Firm* — Schwegman, Lundberg & Woessner, P.A.

(57) ABSTRACT

In some embodiments, apparatus and systems, as well as methods, may operate to acquire signature data representing a plurality of nuclear magnetic resonance (NMR) echo trains associated with a material comprising a first fluid and a second fluid, force a subset of the signature data associated with the first fluid or the second fluid to correspond to single-peak signatures in the T1 and/or T2 domains, and solve for the first fluid and second fluid saturation. The first fluid may include oil, gas, or water and the second fluid may include oil-based mud filtrate or water-based mud filtrate, among others.

27 Claims, 7 Drawing Sheets

US 8,174,262 B2

FLUID SATURATION ESTIMATION

RELATED APPLICATIONS

This application is a U.S. National Stage Filing under 35 U.S.C. 371 from International Application Number PCT/US2006/028621, filed Jul. 21, 2006 and published in English as WO 2008/010810 A1 on Jan. 24, 2008, which application and publication are incorporated herein by reference in their entirety.

TECHNICAL FIELD

Various embodiments described herein relate to the characterization of different types of matter, including apparatus, systems, and methods used to determine levels of fluid saturation and contamination.

BACKGROUND INFORMATION

Fluids (e.g., oil, water, gas) may exist in a variety of materials, including geological formations. It is often useful to determine the saturation level of a fluid, or of multiple fluids, where one fluid is contaminated by another. However, most available contamination models, such as the nuclear magnetic resonance (NMR)-based models used in the petroleum recovery industry, are designed for miscible fluids (single phase), and may fail when used in immiscible cases. Secondary measurements, such as fluid capacitance and resistivity (which are not always reliable), are sometimes used to refine the estimates derived from the models.

DETAILED DESCRIPTION

Figure 1A:
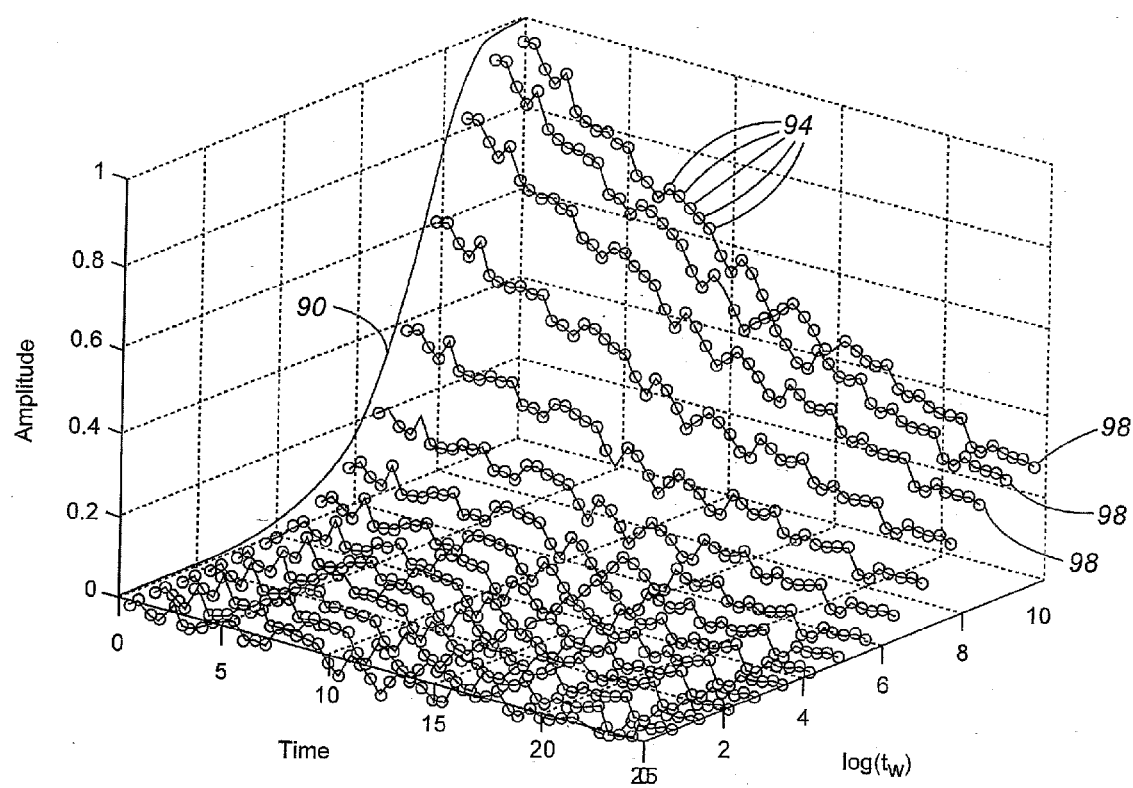
FIG. 1A illustrates estimating time-zero echo amplitude on a $T_1$ buildup curve according to various embodiments of the invention.

In some embodiments of the invention, the challenges described above may be addressed by using nuclear magnetic resonance (NMR) measurements to acquire fluid signature data from a selected material (perhaps comprising immiscible fluids) in the form of echo train information. Optionally thereafter, the time-zero amplitude on a $T_1$ (longitudinal relaxation time) buildup curve may be estimated for each set of acquired echo trains. Then, either the acquired signature data, or the estimated $T_1$ buildup curve associated with the fluid mixture in the material may be used to estimate the saturation of the fluids in the mixture by solving a constrained equation with a reduced number of unknowns.

As a result, a new estimate of signature data (or the $T_1$ buildup curve data) for the selected fluid (e.g., a first fluid), as well as that for a second fluid, may be obtained. The estimates derived in this manner may be used to more accurately determine saturation levels in a material, and to derive a number of fluid properties, so that decisions made with regard to activities conducted at a petroleum recovery site, for example, can be made with increased confidence.

For the purposes of this document, a "fluid" is any material that has an NMR transverse relaxation time constant (e.g., $T_2$) of greater than 1 millisecond. It should also be understood that "saturation" as used herein is the same as the concentration of a fluid, such that a 0.75 saturation of water means that the fluid mixture in question comprises 75 vol % water. As another example, if oil is the native fluid in a formation, a 0.75 water saturation implies a 0.75 contamination fraction, which means that the fluid comprising 75 vol % water also comprises 25 vol % of oil. Further, while materials comprising native and non-native fluids, as such are understood by those of skill in the art in the petroleum recovery industry, may be discussed specifically herein, it should be noted that the mechanisms disclosed are applicable to a much wider variety of fluid types and combinations, and thus, the various embodiments are not to be so limited. Therefore, the term "native fluid" may be used interchangeably with "first fluid", and the term "non-native fluid" may be used interchangeably with "second fluid" throughout this disclosure.

The following variables are defined for the purposes of this document:
c=contamination fraction [unitless]
i=index for the sequence number [unitless]
j=index for the echo number [unitless]
$n_E$=number of acquired echoes for each wait time [unitless]
$n_{tW}$=number of wait times used in the acquisition [unitless]
m=number of data sequences acquired (e.g., while pumping fluid through a fluid analysis tool at the same station depth) [unitless]
$t_E$=echo spacing [ms]
$t_W$=wait time [ms]
$T_1$=longitudinal relaxation time [ms]
$T_2$=transverse relaxation time [ms]
X=$T_1$ buildup curve of non-native fluid [unitless]
Y=$T_1$ buildup curve of native fluid [unitless]
Z=$T_1$ buildup curve of measured echoes [unitless]

FIG. 1A illustrates estimating time-zero echo amplitudes on a $T_1$ buildup curve 90 according to various embodiments of the invention. In this measurement context, a data sequence 94 can be defined as one NMR $T_1$ measurement, comprising $n_{tw}$ wait times $t_W$ resulting in different polarization levels on the $T_1$ buildup curve 90. After each wait time $t_W$, $n_E$ echoes may be acquired with an echo spacing of $t_E$, resulting in an echo train 98. Each of these echo trains 98 can be used to retrieve the echoes on the $T_1$ buildup curve 90 (e.g., time-zero echoes) via standard linear $T_2$ inversion procedures.

For purposes of spatial economy, the process of linear inversion will not be discussed in detail, as it is well known to those of ordinary skill in the art. However, readers that desire to learn more about how $T_2$ distributions can be estimated from a single echo train (as a standard least-squares problem) may consult "NMR Pore Size Distributions and Permeability at the Well Site" by Prammer, SPE paper 28368, 69$^{th}$ Annual Technical Conference and Exhibition, New Orleans, La., 1994; "Practical Optimization," by Gill et al., Academic Press, London and New York (1981); and the "User's guide for LSSOL (version 1.0): A Fortran package for Constrained Linear Least-Squares and Convex Quadratic Programming," by Gill et al., Technical Report SOL 86-1, Systems Optimization Laboratory, Dept. of Operations Research, Stanford University, 1986.

For immiscible fluids, the $T_1$ buildup curve 90 (perhaps represented by a vector Z) at each data sequence is related to the $T_1$ buildup curves of a first fluid (e.g., native fluid) Y and everything that is not the first fluid (e.g., the second fluid, including a non-native fluid, such as a mud filtrate) X in the following way:

$$\begin{bmatrix} Z_1 \\ Z_2 \\ \ldots \\ Z_m \end{bmatrix} = \begin{bmatrix} c_1 X_1 + (1-c_1)Y_1 \\ c_2 X_2 + (1-c_2)Y_2 \\ \ldots \\ c_m X_m + (1-c_m)Y_m \end{bmatrix}, \quad (1)$$

where $0 \leq c_i \leq 1$ denotes the contamination fraction and m denotes the number of data sequences acquired (e.g., while pumping fluid through an NMR fluid analysis tool, perhaps at the same station depth). That is, $Z_i = c_i X_i + (1-c_i) Y_i$, where Y represents the first fluid (e.g., the native fluid, such as oil, gas, or water), and X represents the second fluid (e.g., the non-native fluid, such as an oil-based mud filtrate or water-based mud filtrate) in a material.

Note that if Z represents the $T_1$ buildup curve, then the following relationships may be observed: $Z_i \in \Re^{n_{tW} \times 1}$, $X_i \in \Re^{n_{tW} \times 1}$, $Y_i \in \Re^{n_{tW} \times 1}$, such that each of the Z's, X's, and Y's are vectors of length $n_{tW}$. If Z represents the acquired signature data, and if each acquired echo train has an equal number of echoes, $Z_i \in \Re^{n_{tW} n_E \times 1}$, $X_i \in \Re^{n_{tW} n_E \times 1}$, $Y_i \in \Re^{n_{tW} n_E \times 1}$ and each of the Z's, X's, and Y's are then vectors of length $n_{tW} n_E$. From now on we will focus on the case where Z represents the $T_1$ buildup curve. As is known to those of skill in the art, $\Re$ is the mathematical notation for a set of real-valued numbers (i.e., the numbers are not in complex form). Thus, for example, $Y \in \Re^{n_{tW} \times 1}$ comprises a real-valued matrix with $n_{tW}$ rows and 1 column (a vector).

To solve equation (1), consider that $X_i$ may represent unknowns comprising the echo time-zero signatures of the non-native fluid at each sequence. Since the signature of the native fluid may be considered as substantially constant during pumping operations, the subscript' on Y can be dropped and equation (1) can be rewritten as:

$$\begin{bmatrix} Z_1 \\ Z_2 \\ \ldots \\ Z_m \end{bmatrix} = \begin{bmatrix} c_1 X_1 + (1-c_1)Y \\ c_2 X_2 + (1-c_2)Y \\ \ldots \\ c_m X_m + (1-c_m)Y \end{bmatrix}. \quad (2)$$

$X_i$ may then be allowed to vary from sequence to sequence, so that potential effects of fines in the flowline (which can appear sporadically during pumping operations) and flow-effects on the echoes (which may occur when the magnitude of $T_1$ is relatively large, and/or fluid velocity is relatively high) can be accounted for implicitly. As those of skill in the art are aware, fines may comprise small sand particles that can enter the measurement tool while pumping fluid from the formation.

It can now be seen that the nonlinear system represented by equation (2) is underdetermined, since the number of unknowns ($c_i$, $X_i$, and Y) is $(m+1)*n_{tW}+m$, whereas the number of measured data points is $m*n_{tW}$. For example, if the dataset includes 100 sequences using 15 wait times, the number of equations is 1500 and the number of unknowns is 1615. Solving nonlinear, underdetermined problems can be very difficult, and even infeasible in the commercial context considering the signal-to-noise ratio of the data and the potential requirement to detect the volumetric amounts of multiple fluid components in a material where some components exist in relatively small quantities.

Nonetheless, equation (2) may be solved with a useful degree of accuracy by constraining the mathematical problem and reducing the number of unknowns. That is, constraints may be added to force the signatures $X_i$ to correspond to single-peak signatures $T_{1X_i}$ in the $T_1$ domain. Since the second fluid, including non-native fluids such as mud filtrates, typically exhibits single-peak $T_1$ distributions, this assumption is usually valid unless, for example, the second fluid has been recycled a number of times during drilling operations. The assumption may also be valid in the presence of fines and high flow rates, since neither of these disturbances typically contribute to additional peaks in the $T_1$ distribution.

Constraining the signatures $X_i$ to correspond to single-peak $T_1$ signatures amounts to adding $m*n_{tw}$ nonlinear constraints, reducing the total number of unknowns to $n_{tw}+2m$. Again, assuming 100 data sequences and 15 wait times, there are still 1500 equations, but now only 215 unknowns. It can be shown that the problem becomes overdetermined when the conditions m>2 and $n_{tw}$>4 are satisfied, which is usually the case in practical situations.

Given the foregoing assumptions, and constraining the signatures $X_i$, the problem can now be cast in a constrained nonlinear least-squares form, having a solution that provides substantially optimal values for the unknowns: Y, $T_{1X1}$, $T_{1X2}$, ..., $T_{1Xm}$, and $c_1, c_2, \ldots, c_m$. That is:

$$\min \frac{1}{2} \left\| \begin{matrix} Z_1 - c_1 X_1 + (1-c_1)Y \\ Z_2 - c_2 X_2 + (1-c_2)Y \\ \ldots \\ Z_m - c_m X_m + (1-c_m)Y \end{matrix} \right\|_2^2, \quad (3)$$

subject to the constraints of $$\begin{bmatrix} X_1(j) \\ X_2(j) \\ \ldots \\ X_m(j) \end{bmatrix} = \begin{bmatrix} 1 - e^{-tw_j/T_{1X_1}} \\ 1 - e^{-tw_j/T_{1X_2}} \\ \ldots \\ 1 - e^{-tw_j/T_{1X_m}} \end{bmatrix},$$

where $j=1, \ldots, n_{tw}$. This is how the signatures of the second (e.g. non-native) fluid may be forced to correspond to single peak signatures.

Solving Equation (3) for Y, $T_{1X}$, and c can be readily done with any nonlinear constrained optimization solver. For purposes of spatial economy, the process of nonlinear inversion will not be discussed in detail, as it is well known to those of ordinary skill in the art. However, readers that desire to learn more about how to solve nonlinear, constrained optimization problems may consult "User's guide for NPSOL 5.0: A Fortran package for Nonlinear Programming," by Gill et al., Technical Report SOL 86-2, Systems Optimization Laboratory, Dept. of Operations Research, Stanford University, 1998.

As an alternative solution method, an iterative procedure involving the following activities may be used:
(a) use any method to make an initial guess for c,
(b) solve equation (3) for Y and $T_{1X}$, using c fixed as the initial guess and the measured values of Z,
(c) use the resulting value of Y to solve a linear program (shown below) for c, and (d) stop if the solution for c converges to the desired degree (e.g., less than 1% difference between prior and current values of c), otherwise
(e) iterate to (b) above, re-solving equation (3) using the new value of c.

The linear program of (c) above may be developed by re-writing equation (2) in the following form:

$$\begin{bmatrix} Z_1 - (1-c_1)Y \\ Z_2 - (1-c_2)Y \\ \ldots \\ Z_m - (1-c_m)Y \end{bmatrix} = \begin{bmatrix} c_1 X_1 \\ c_2 X_2 \\ \ldots \\ c_m X_m \end{bmatrix}. \quad (4)$$

Finding a solution to equation (4) may be considered substantially the same as solving the following linear program:

$$\min_{0 \leq c_i \leq 1} c_i,$$

subject to $$\begin{bmatrix} Z_i(1) - (1-c_i)Y(1) \\ Z_i(2) - (1-c_i)Y(2) \\ \ldots \\ Z_i(n_tW) - (1-c_i)Y(n_tW) \end{bmatrix} \geq \begin{bmatrix} 0 \\ 0 \\ \ldots \\ 0 \end{bmatrix} \quad (5)$$

for each sequence i=1, . . . , m. Note that equation (5), as set forth above, is independent of the signatures $X_i$.

Once the contamination fraction c has been determined according to either of the two proposed methods above, the saturation of the first fluid (Y) and the second fluid (X) can be readily found. If for example c=0.75 then the saturation of the first fluid is 25 vol % and the saturation of the second fluid is 75 vol %.

Figure 1B:
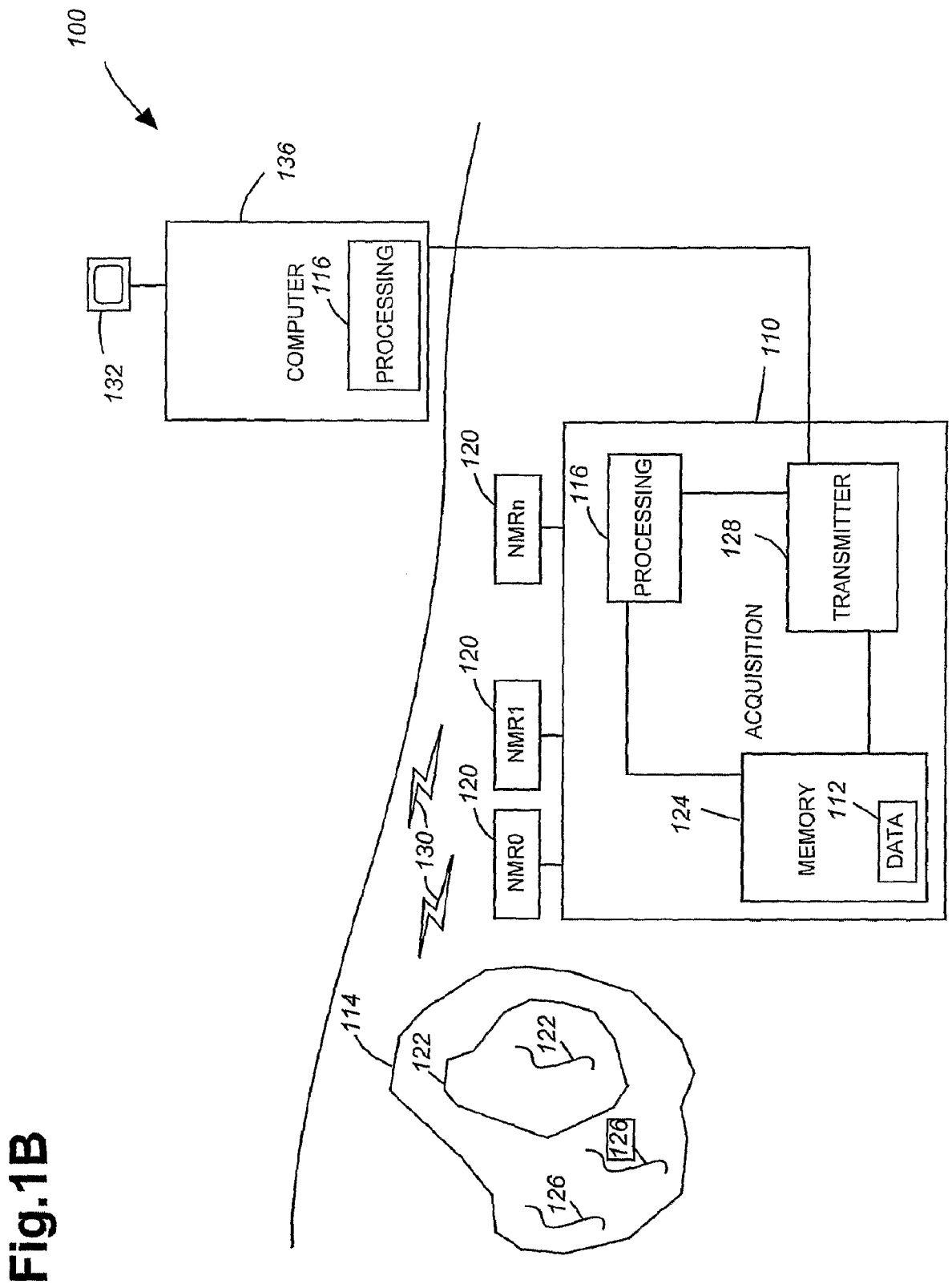
FIG. 1B illustrates an apparatus according to various embodiments of the invention.

To implement the solutions just described, a variety of apparatus, systems, and methods may be used. For example, FIG. 1B illustrates an apparatus 100 according to various embodiments of the invention. In some embodiments, the saturation estimation apparatus 100 may include acquisition logic 110 to acquire data 112 (e.g., measured signature data Z) representing a plurality of NMR echo trains associated with a material 114 comprising a first fluid 122 and a second fluid 126. The apparatus 100 may also include processing logic 116 to force a subset of the data associated with at least one of the first fluid 122 and the second fluid 126 to correspond to single-peak signatures in the $T_1$ and/or $T_2$ domains. The processing logic 116 may also operate to solve for the saturation of the first fluid and/or the second fluid. In some embodiments, the first and second fluids may comprise a native fluid and a non-native fluid, respectively.

In some embodiments, the apparatus 100 may include one or more NMR sensors 120 to receive signals 130 associated with the data 112. The apparatus 100 may also include a memory 124 to store the data 112. In some embodiments, the processing logic 116 may operate to compute time-zero echoes using a linear $T_2$ inversion of the data 112, as described above. The processing logic 116 may be, included in a downhole tool, or above-ground (e.g., as part of an above-ground computer workstation, perhaps located in a logging facility), or both.

In some embodiments, the apparatus 100 may include one or more telemetry transmitters 128 to transmit the data 112 to an above-ground computer 136. The apparatus 100 may also include one or more displays 132 to display visual representations of the saturation, contamination, and/or fluid characteristics derived therefrom, including the $T_1$ spectra of the first and second fluids in the fluid mixture.

In some embodiments, the volumetric fraction of native fluids may thus be estimated, perhaps using $T_1$ spectrum data provided by a formation tester, such as the Reservoir Description Tool (RDT™), available from the Halliburton Company's Energy Services Group, using a downhole NMR fluid analysis tool, including the integrated MRILab® service provided by Halliburton Energy Services. Since contaminates mixed with crude oil can modulate the $T_1$ response, such $T_1$ measurements can be interpreted to determine when a clean sample can be taken and saved in a downhole tool sample chamber (e.g., a Halliburton Reservoir Description Tool (RDT™) sample chamber).

Figure 2A:
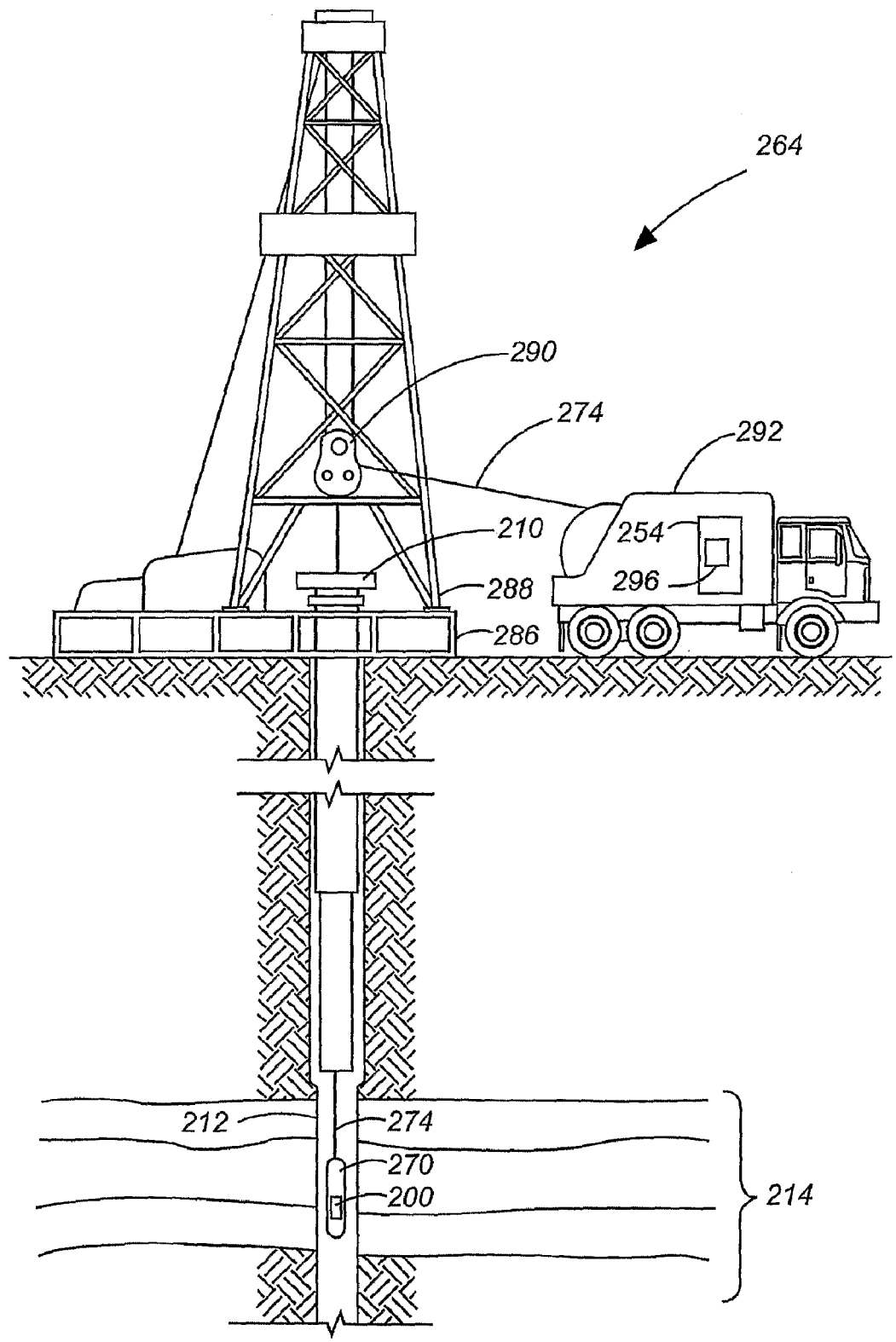
FIGS. 2A-2B illustrate apparatus and systems according to various embodiments of the invention.
Figure 2B:
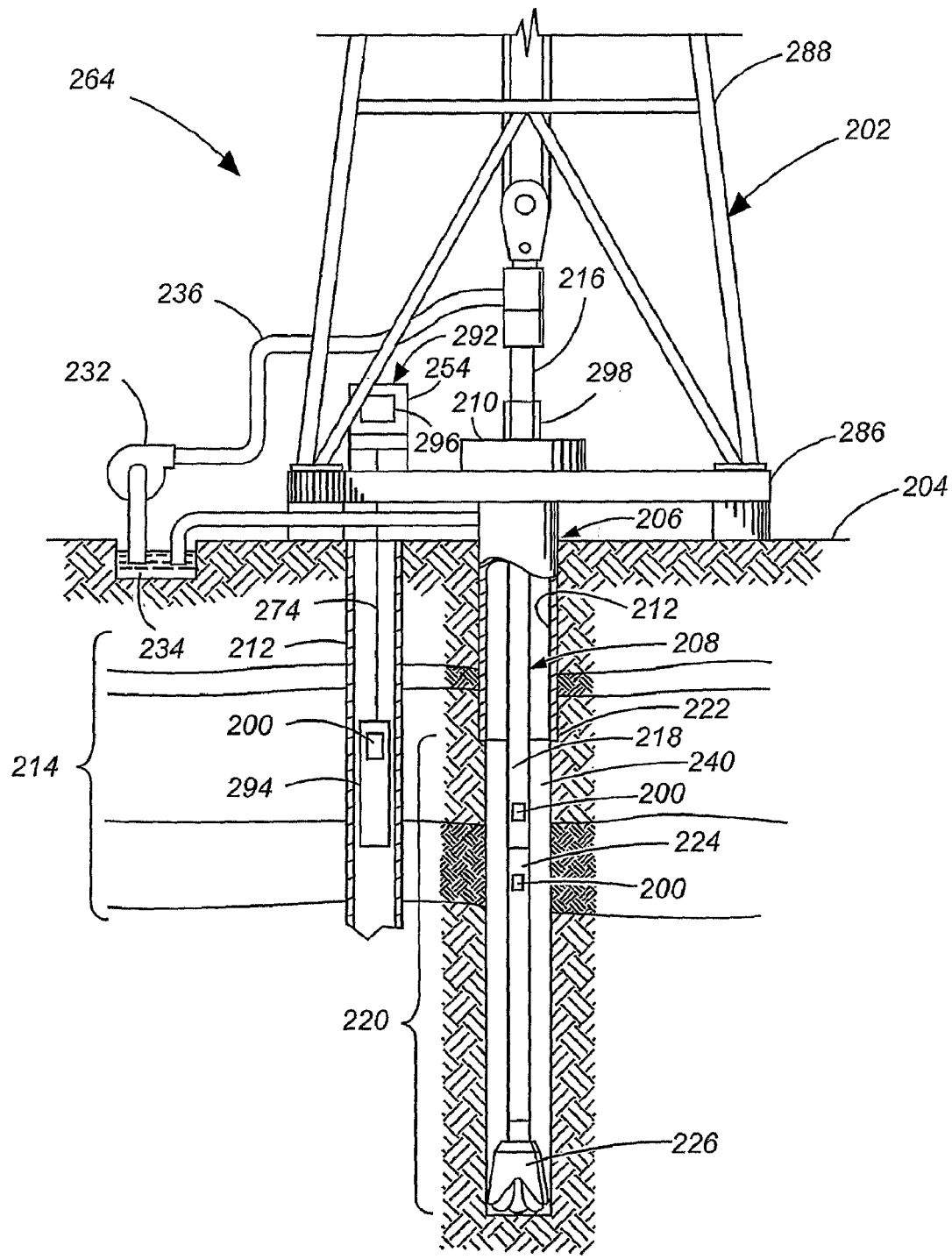

FIGS. 2A-2B illustrate apparatus 200 and systems 264 according to various embodiments of the invention. The apparatus 200, which may be similar to or identical to the apparatus 100 described above and shown in FIG. 1B, may comprise portions of a tool body 270 as part of a wireline logging operation, or of a downhole tool 224 as part of a downhole drilling operation. For example, FIG. 2A shows a well during wireline logging operations. A drilling platform 286 may be equipped with a derrick 288 that supports a hoist 290. Oil and gas well drilling operations are commonly carried out using a string of drill pipes connected together so as to form a drilling string that is lowered through a rotary table 210 into a wellbore or borehole 212.

Here it is assumed that the drilling string has been temporarily removed from the borehole 212 to allow a tool body 270 (e.g., a wireline logging tool), such as a probe or sonde, to be lowered by wireline or logging cable 274 into the borehole 212. Typically, the tool body 270 is lowered to the bottom of the region of interest and subsequently pulled upward at a substantially constant speed. During the upward trip, instruments included in the tool body 270 (e.g., apparatus 200) may be used to perform measurements on the subsurface formations 214 adjacent the borehole 212 as they pass by, or as the tool body 270 remains stationary.

Measurement data (e.g., similar or identical to data 112 of FIG. 1B) may include NMR echo train data that can be communicated to a logging facility 292 for storage, processing, and analysis. The logging facility 292 may be provided with electronic equipment for various types of signal processing. Similar log data may be gathered and analyzed during drilling operations (e.g., during logging while drilling (LWD) operations). For example, the tool body 270 in this case may house one or more apparatus 200, and the logging facility 292 may include one or more surface computers 254, similar to or identical to the computer 136 described above with respect to FIG. 1.

Turning now to FIG. 2B, it can be seen how a system 264 may also form a portion of a drilling rig 202 located at a surface 204 of a well 206. The drilling rig 202 may provide support for a drill string 208. The drill string 208 may operate to penetrate a rotary table 210 for drilling a borehole 212 through subsurface formations 214. The drill string 208 may include a Kelly 216, drill pipe 218, and a bottom hole assembly 220, perhaps located at the lower portion of the drill pipe 218. The drill string 208 may include wired and unwired drill pipe, as well as wired and unwired coiled tubing, including segmented drilling pipe, casing, and coiled tubing.

The bottom hole assembly 220 may include drill collars 222, a downhole tool 224, and a drill bit 226. The drill bit 226 may operate to create a borehole 212 by penetrating the surface 204 and subsurface formations 214. The downhole tool 224 may comprise any of a number of different types of tools including measurement while drilling (MWD) tools, LWD tools, and others.

During drilling operations, the drill string 208 (perhaps including the Kelly 216, the drill pipe 218, and the bottom hole assembly 220) may be rotated by the rotary table 210. In addition to, or alternatively, the bottom hole assembly 220 may also be rotated by a motor (e.g., a mud motor) that is located downhole. The drill collars 222 may be used to add weight to the drill bit 226. The drill collars 222 also may stiffen the bottom hole assembly 220 to allow the bottom hole assembly 220 to transfer the added weight to the drill bit 226, and in turn, assist the drill bit 226 in penetrating the surface 204 and subsurface formations 214.

During drilling operations, a mud pump 232 may pump drilling fluid (sometimes known by those of skill in the art as "drilling mud") from a mud pit 234 through a hose 236 into the drill pipe 218 and down to the drill bit 226. The drilling fluid can flow out from the drill bit 226 and be returned to the surface 204 through an annular area 240 between the drill pipe 218 and the sides of the borehole 212. The drilling fluid may then be returned to the mud pit 234, where such fluid is filtered. In some embodiments, the drilling fluid can be used to cool the drill bit 226, as well as to provide lubrication for the drill bit 226 during drilling operations. Additionally, the drilling fluid may be used to remove subsurface formation 214 cuttings created by operating the drill bit 226.

Thus, referring now to FIGS. 1A and 2A-2B, it may be seen that in some embodiments, the system 264 may include a drill collar 222, and/or a downhole tool 224, including a tool body 270 or a substantially permanently installed probe 294 (in a downhole well), to which one or more apparatus 200 are attached. The downhole tool 224 may comprise an LWD tool or MWD tool. The tool body 270 may comprise a wireline logging tool, including a probe or sonde, for example, coupled to a cable 274, such as a wireline or logging cable. Thus, a wireline 274 or a drill string 208 may be mechanically coupled to the downhole tool 224.

In some embodiments then, a system 264, such as a saturation determination system, may include a downhole tool 270 and acquisition logic 110 as described above and shown in FIG. 1. The acquisition logic 110, as well as any other part of the apparatus 100, 200, including the processing logic 116, may be housed by the downhole tool 270.

In some embodiments, the system 264 may include a drill bit 226 mechanically coupled to a drill string 208 and the downhole tool 224. The drill string may include one or more of segmented drilling pipe, casing, and/or coiled tubing. The system 264 may further include a steering mechanism 298 to steer the drill bit 226 responsive to the saturation, contamination, and/or any number of fluid characteristics that may be determined as a result of determining the saturation. In some embodiments, the apparatus 200 may be applied to determine when the first fluid is substantially clean so that measured properties may be attributed to the first fluid with some degree of confidence. Thus, the saturation may also be used to determine when a fluid sample should be taken at a particular downhole elevation during wireline operations before moving on to a different depth.

In some embodiments, the system 264 may include one or more displays 296 to display visual representations of the saturation, contamination, and a variety of fluid characteristics such as the estimated $T_1$ spectrum of the native and non-native fluids. The display 296 may be included as part of a surface computer 254 used to receive data from the acquisition logic 110, if desired.

The apparatus $T_1$ buildup curve 90; data sequences 94; echo trains 98; apparatus 100, 200; acquisition logic 110; data 112; material 114; processing logic 116; NMR sensors 120; first fluid 122; memory 124; second fluid 126; telemetry transmitter 128; signals 130; computers 136, 254; displays 132, 296; drilling rig 202; surface 204; well 206; drill string 208; rotary table 210; borehole 212; formations 214; Kelly 216; drill pipe 218; bottom hole assembly 220; drill collars 222; downhole tool 224; drill bit 226; mud pump 232; mud pit 234; hose 236; annular area 240; systems 264; tool body 270; wireline 274; drilling platform 286; derrick 288; hoist 290; logging facility 292; probe 294; and steering mechanism 298 may all be characterized as "modules" herein. Such modules may include hardware circuitry, and/or a processor and/or memory circuits, software program modules and objects, and/or firmware, and combinations thereof, as desired by the architect of the apparatus 100, 200 and systems 264, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for drilling and logging operations, and thus, various embodiments are not to be so limited. The illustrations of apparatus 100, 200 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules, including multilayer, multi-chip modules. Such apparatus and systems may further be included as sub-components within a variety of electronic systems, such as process measurement instruments, personal computers, workstations, medical devices, vehicles, among others. Some embodiments include a number of methods.

Figure 3:
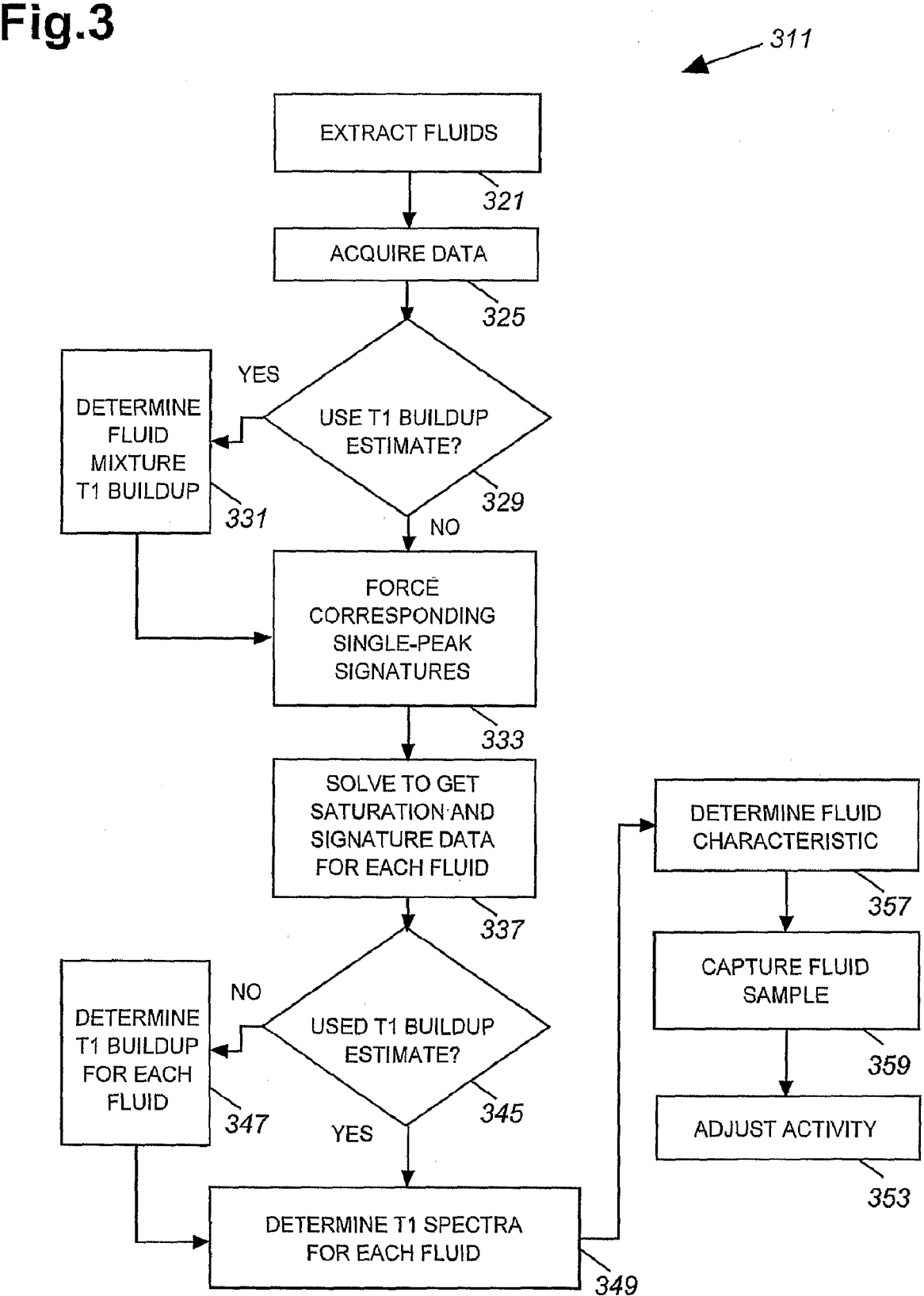
FIG. 3 illustrates a method flow diagram according to various embodiments of the invention.

For example, FIG. 3 illustrates a method flow diagram 311 according to various embodiments of the invention. In some embodiments of the invention, a method 311, such as a method of estimating the saturation of fluids in a material, may begin at block 321 with extracting the mixture of the first and second fluids included in a material, such as a geological formation, from the material. As noted previously, the first fluid may comprise one or more of oil, water, and gas, and the second fluid may comprise one or more of an oil-based mud filtrate and a water-based mud filtrate. Of course, other fluid combinations are possible.

In some embodiments, the method 311 may include acquiring data, such as signature data (Z), representing a plurality of NMR echo trains associated with the material comprising the first fluid and the second fluid at block 325. The material may include one or more fluids, or the fluids may have been withdrawn from the material. The data may be acquired as a portion of acquiring a larger data set during the conduct of an NMR measurement process.

In some embodiments, the method 311 may include determining whether to use a $T_1$ buildup estimate for the mixture of the fluids at block 329. Thus, the method 311 may include transforming from the signature data domain to the $T_1$ buildup domain at this point. If this occurs, then transformation to the $T_1$ domain after inversion (as part of the activities described below for block 347) may be unnecessary. Therefore, if the choice is made to use a $T_1$ buildup estimate for the mixture of fluids at block 329, the method may continue at block 331 with determining the fluid mixture $T_1$ buildup, perhaps by fitting the signature data to provide an estimated amplitude on a $T_1$ buildup curve. As noted previously, solving for Y may provide an estimate of time-zero echoes, which may be inverted to provide a $T_1$ spectrum of the first fluid (e.g., the native fluid). In fact, the $T_1$ spectrum may be obtained for the mixture of the first and second fluids. If the choice is made not to use a $T_1$ buildup estimate for the fluid mixture at block 329, then the method may continue at block 333.

Equation (3), described above, is used in some embodiments to estimate the signature of each of the fluids in the time domain, as well as to provide the saturation of each fluid. In other words, the echoes of each fluid may be predicted substantially as if the original measurements were made of each fluid individually—without contamination. The saturations of each fluid may also be determined, and then $T_2$ and/or $T_1$ inversions may be implemented to provide the $T_1$ spectrum for each fluid. If Z is assigned to the original fluid measurements (obtained at block 325), instead of the time-zero echoes estimated at block 331, then both $T_1$ and $T_2$ spectra can be determined.

Thus, in some embodiments, the method 311 may include measuring to acquire echo data (e.g., at block 325), which comprises signature data for the fluid mixture (comprising the first and second fluids). The method 311 may then optionally include at block 331 implementing a $T_2$ inversion, which provides an estimate of the amplitude on $T_1$ buildup curve for each wait time (e.g., each set of signature data). Thus, the method 311 may include computing time-zero echoes using a linear $T_2$ inversion of the signature data. That is, equation (3) may be solved using either original measurements, or time-zero echoes. If original measurements are used, then $T_1$ and $T_2$ for both fluids may be determined, provided sufficient data was acquired to fully resolve the $T_2$ information. However, taking this path may result in a more difficult problem to solve, requiring substantially more processing time.

In some embodiments, the method 311 may include, at block 333, forcing a subset of the signature data associated with the first fluid and/or the second fluid to correspond to single-peak signatures in the $T_1$ and/or $T_2$ domains. The method 311 may also include taking either acquired signature data, or estimated $T_1$ buildup curve data, and assigning the Z vector to one of these, and then solving equation (3) to obtain the saturation and signature data of one or both of the fluids at block 337.

Additional data that may result from solving equation (3) includes an estimate of approximately what the signature data might be for the first and second fluids, or an estimate of the $T_1$ buildup curve if the estimate was used at block 329. This may then comprise a substantially constant signature estimate associated with each of the fluids.

Depending on whether the $T_1$ buildup curve estimate was used to solve equation (3), as determined at block 345, the method 311 may include a variety of activities. For example, if measured signature data was used to solve equation (3), instead of estimated $T_1$ buildup curve data, then the method 311 may include determining an estimate of the $T_1$ buildup curve data for each fluid at block 347. Then the method 311 may continue at block 349. Thus, if the measured signature data is used as Z, then a first activity may include performing a linear $T_2$ inversion based on both X and Y to compute the $T_2$ spectra (and therefore also the $T_1$ buildup curve) of X and Y at block 347, and a second activity may include performing a linear $T_1$ inversion based on the $T_1$ buildup curve to estimate the $T_1$ spectra of X and Y at block 349. On the other hand, if the $T_1$ buildup curve for the fluid mixture is used as Z instead of the measured signature data, then the first activity may be skipped (at block 347), and the method 311 may go on to the second activity at block 349.

In some embodiments, the method 311 may include providing an initial estimate of the saturation, and then iteratively solving for a substantially constant signature estimate associated with the first fluid and a relaxation time of the second fluid at each sequence of the signature data until the saturation converges to a specified tolerance. Iteratively solving may include solving for the converging saturation using the substantially constant signature estimate associated with the first fluid, the relaxation time of the second fluid (determined previously), and the (measured) signature data (Z). Alternatively, in some embodiments, the method 311 may include solving for a substantially constant signature estimate associated with the first fluid and relaxation time of the second fluid at each sequence and the saturation using a non-linear least-squares approach.

In some embodiments, the method 311 may include determining a fluid characteristic at block 357. For example, the fluid characteristic may comprise viscosity, diffusion, as well as other characteristics. Thus the method 311 may include determining the viscosity of the first fluid using the substantially constant signature estimate associated with the first fluid. This is because a relationship between the log mean of $T_1$ and viscosity can be derived, and the average value of $T_1$, or the log mean of $T_1$ may be used to determine viscosity.

In some embodiments, the method 311 may include determining whether a fluid sample should be captured based on the determined saturation, and then capturing a fluid sample at block 359. Thus, the method 311 may include determining whether to capture a fluid sample based on prior values of the saturation. In some embodiments, the method 311 may include adjusting the conduct of a formation testing activity based on the fluid characteristic in substantially real time. This may take the form of adjusting the pump rate at which the fluid mixture is being withdrawn from the formation, steering a drill bit, or adjusting drilling depth based on determined fluid characteristics and/or and fluid properties determined from a $T_1$ spectrum of the first fluid, at block 363.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received, and perhaps stored using a variety of media, tangible and intangible, including one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 4:
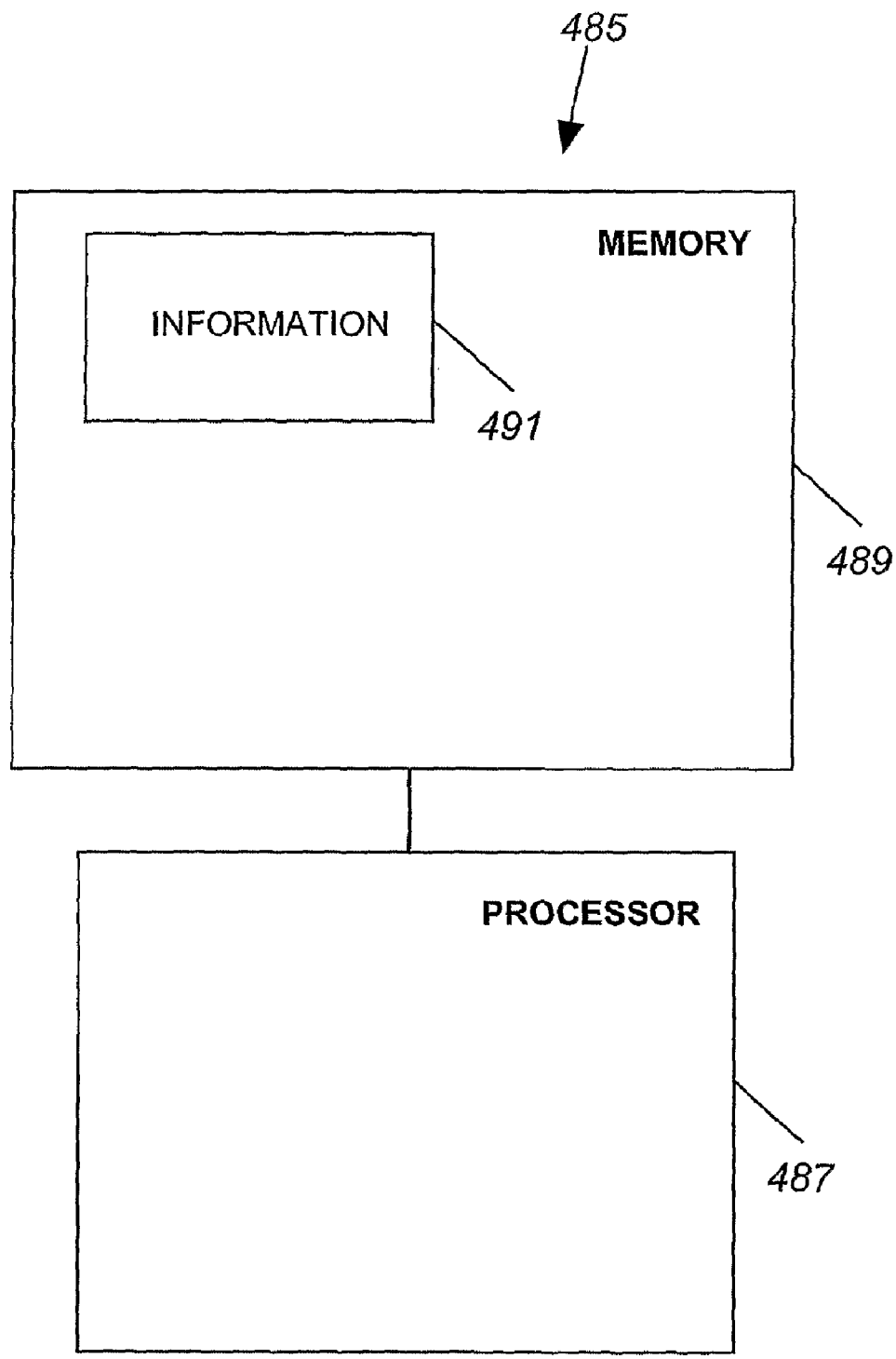
FIG. 4 is a block diagram of an article according to various embodiments of the invention.

FIG. 4 is a block diagram of an article of manufacture, or article 485 according to various embodiments, such as a computer, a memory system, a magnetic or optical disk, some other storage device, and/or any type of electronic device or system. The article 485 may include a processor 487 coupled to a computer-readable medium such as a memory 489 (e.g., fixed and removable storage media, including tangible memory having electrical, optical, or electromagnetic conductors; or even intangible memory, such as a carrier wave) having associated information 491 (e.g., computer program instructions and/or data), which when executed by a computer, causes the computer (e.g., the processor 487) to perform a method including such actions as acquiring signature data (Z) representing a plurality of NMR echo trains associated with a material comprising a first fluid and a second fluid, forcing a subset of the signature data associated with one or both of the fluids to correspond to single-peak signatures in the $T_1$ and/or T2 domains, and solving for the saturation of at least one of the fluids.

Other activities may include determining fluid characteristics of the first fluid using the substantially constant signature estimate associated with the first fluid, and adjusting conduct of a formation testing activity based on the fluid characteristic in substantially real time. Further activities may include solving for the saturation, and determining whether to capture a fluid sample based on prior values of the saturation. In fact, any of the activities described with respect to the various methods above may be implemented in this manner.

Figure 5A:
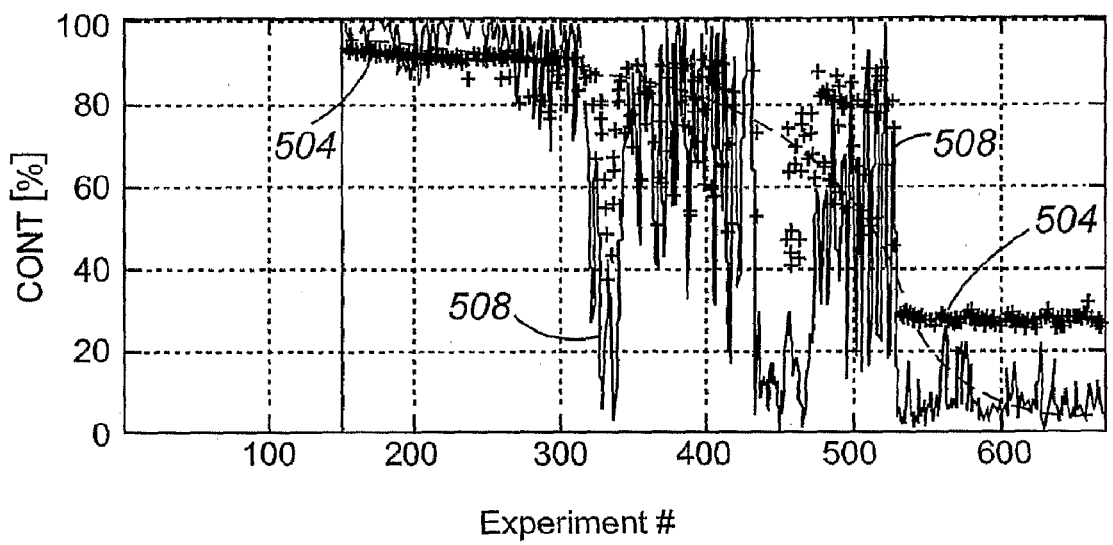
FIGS. 5A-5B illustrate an example of computing saturation/contamination, and the resulting $T_1$ distributions, respectively, according to various embodiments of the invention.
Figure 5B:
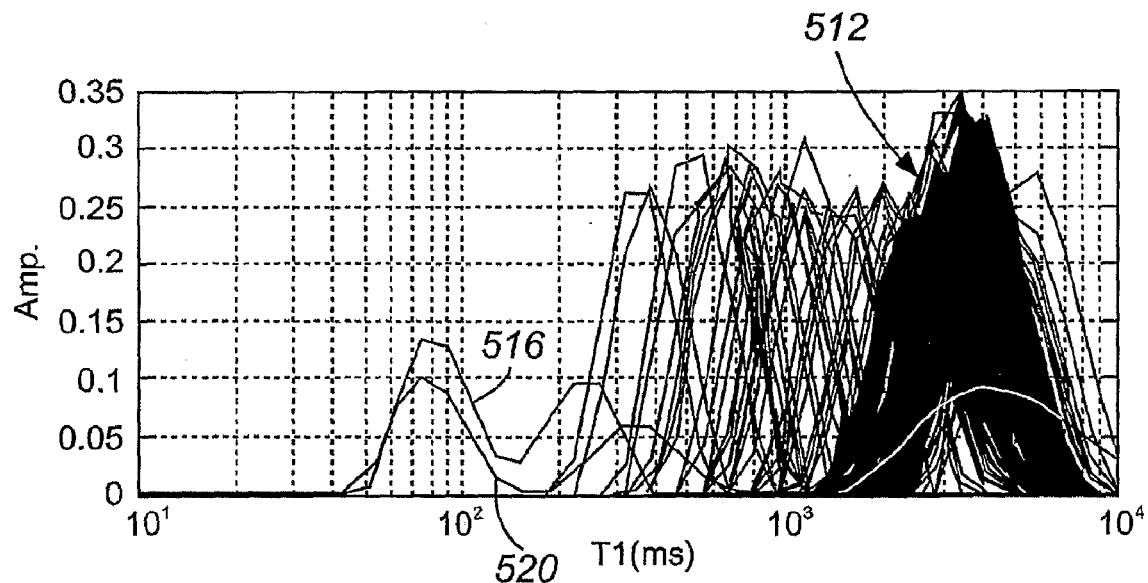

To further demonstrate the benefits of the disclosed apparatus, systems, and methods, an example implementation will now be discussed. FIGS. 5A-5B illustrate an example of computing saturation/contamination, and the resulting $T_1$ distributions, respectively, according to various embodiments of the invention.

After acquiring NMR echo data from a well, equation (3) was solved and resulted in the calculated contamination curve 504 in FIG. 5A. This can be compared with the contamination result curve 508 provided by an existing FluidXpert software program, designed to be used with miscible fluids. Readers that desire to know more about existing methods of estimating miscible fluid contamination can consult "Fluid Sampling and Interpretation with the Downhole NMR Fluid Analyzer," Akkurt et. al, paper 90971, SPE Annual Technical Conference and Exhibition, Houston, Tex., 2004, incorporated herein by reference in its entirety. The resulting $T_1$ distribution for the second fluid (Xi) 512 corresponding to the calculated contamination curve 504 are shown in FIG. 5B. The $T_1$ distribution 516 for the first fluid 516 (here being native oil) is also displayed, along with the $T_1$ distribution corresponding to the last sequence number 520. The result is a contamination estimate of about 60%, which is well in agreement with the 56% reported from a laboratory analysis. The contamination estimate, after pumping was stopped (resulting in fluid segregation), remained at a reasonable and fairly constant 28%.

Implementing the apparatus, systems, and methods of various embodiments may improve the accuracy of estimating saturation and contamination of fluids, including immiscible fluids and fluids recovered from geological formations. Thus, estimates of saturation may be arrived at with greater confidence in a variety of situations.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, including:
    acquisition logic to acquire signature data representing a plurality of nuclear magnetic resonance (NMR) echo trains associated with a material comprising a first fluid and a second fluid; and
    processing logic to force a subset of the signature data associated with at least one of the first fluid and the second fluid to correspond to single-peak signatures in the $T_1$ and/or $T_2$ domains, and to solve for a saturation of the at least one of the first fluid and the second fluid.

2. The apparatus of claim 1, further including:
    NMR sensors to receive signals associated with the signature data.

3. The apparatus of claim 1, further including:
    a memory to store the signature data.

4. The apparatus of claim 1, wherein the processing logic is to compute time-zero echoes using a linear $T_2$ inversion of the signature data.

5. The apparatus of claim 1, wherein the processing logic is to compute $T_1$ spectra of estimated signature data for the first fluid and the second fluid.

6. The apparatus of claim 1, further including:
a telemetry transmitter to transmit the signature data to an above-ground computer.

7. The apparatus of claim 1, further including:
a display to display visual representations of the saturations and $T_1$ spectra of the first and second fluids in the fluid mixture.

8. A system, including:
a downhole tool;
acquisition logic included in the downhole tool to acquire signature data representing a plurality of nuclear magnetic resonance (NMR) echo trains associated with a material comprising a first fluid and a second fluid; and
processing logic to force a subset of the signature data associated with at least one of the first fluid and the second fluid to correspond to single-peak signatures in the $T_1$ and/or $T_2$ domains, and to solve for a saturation of the at least one of the first fluid and the second fluid.

9. The system of claim 8, wherein the processing logic is included in the downhole tool.

10. The system of claim 8, further including:
a wireline coupled to the downhole tool.

11. The system of claim 8, further including:
a drill bit mechanically coupled to a drill string and the downhole tool; and
a steering mechanism to steer the drill bit responsive to at least one of the saturation and fluid properties determined from a $T_1$ spectrum of the first fluid.

12. The system of claim 11, wherein the drill string includes at least one of segmented drilling pipe, casing, and coiled tubing.

13. A method, including:
acquiring signature data representing a plurality of nuclear magnetic resonance echo trains associated with a material comprising a first fluid and a second fluid;
forcing a subset of the signature data associated with at least one of the first fluid and the second fluid to correspond to single-peak signatures in the $T_1$ and/or $T_2$ domains; and
solving for a saturation of the at least one of the first fluid and the second fluid.

14. The method of claim 13, further including:
fitting the signature data to provide an estimated amplitude on a $T_1$ buildup curve.

15. The method of claim 13, further including:
estimating a $T_1$ spectrum associated with the first fluid and a relaxation time of the second fluid.

16. The method of claim 13, wherein the solving further includes:
providing an initial estimate of the saturation; and
iteratively solving for a substantially constant signature estimate associated with the first fluid and a relaxation time of the second fluid at each sequence of the signature data until the saturation converges to a converging saturation.

17. The method of claim 13, wherein the iteratively solving further includes:
solving for the converging saturation using the substantially constant signature estimate associated with the first fluid, the relaxation time of the second fluid, and the signature data.

18. The method of claim 13, wherein the solving further includes:
solving for a substantially constant signature estimate associated with the first fluid and relaxation time of the second fluid at each sequence and the saturation using a non-linear least-squares approach.

19. The method of claim 13, further including:
extracting the mixture of the first fluid and the second fluid from a geological formation.

20. The method of claim 13, wherein the first fluid comprises a native fluid, and wherein the second fluid comprises a non-native fluid.

21. The method of claim 13, wherein the first fluid comprises at least one of oil, water, and gas, and the second fluid comprises at least one of an oil-based mud filtrate and a water-based mud filtrate.

22. The method of claim 13, further including:
determining the viscosity of the first fluid using the substantially constant signature estimate associated with the first fluid.

23. The method of claim 13, further including:
computing time-zero echoes using a linear $T_2$ inversion of the signature data.

24. A non-transitory computer-readable medium having instructions stored thereon which, when executed by a computer, cause the computer to perform a method comprising:
acquiring signature data representing a plurality of nuclear magnetic resonance echo trains associated with a material comprising a first fluid and a second fluid;
forcing a subset of the signature data associated with at least one of the first fluid and the second fluid to correspond to single-peak signatures in the $T_1$ and/or $T_2$ domains; and
solving for a saturation of the at least one of the first fluid and the second fluid.

25. The non-transitory computer-readable medium of claim 24, wherein the instructions, when executed by the computer, cause the computer to perform a method comprising:
determining a fluid characteristic of the first fluid using the substantially constant signature estimate associated with the first fluid; and
adjusting conduct of a formation testing activity based on the fluid characteristic in substantially real time.

26. The non-transitory computer-readable medium of claim 24 wherein the fluid characteristic comprises one of a viscosity and diffusion.

27. The non-transitory computer-readable medium of claim 24, wherein the instructions, when executed by the computer, cause the computer to perform a method comprising:
determining whether to capture a fluid sample based on a prior value of the saturation.

* * * * *